(12) United States Patent
Zhang et al.

(10) Patent No.: US 11,779,625 B2
(45) Date of Patent: Oct. 10, 2023

(54) COMPOSITION AND APPLICATION THEREOF IN PREPARING PRODUCT FOR PROTECTING MITOCHONDRIA

(71) Applicant: INFINITUS (CHINA) COMPANY LTD., Guangdong (CN)

(72) Inventors: Ying Zhang, Guangdong (CN); Yiting Yang, Guangdong (CN); Jian Tang, Guangdong (CN); Jiaoyan Ren, Guangdong (CN); Min Wang, Guangdong (CN)

(73) Assignee: Infinitus (China) Company Ltd., Guangdong (CN)

( * ) Notice: Subject to any disclaimer, the term of this patent is extended or adjusted under 35 U.S.C. 154(b) by 0 days.

(21) Appl. No.: 17/553,911

(22) Filed: Dec. 17, 2021

(65) Prior Publication Data
US 2023/0072134 A1   Mar. 9, 2023

(30) Foreign Application Priority Data
Aug. 26, 2021  (CN) .......................... 202110990470.7

(51) Int. Cl.
| | | |
|---|---|---|
| *A61K 36/815* | (2006.01) | |
| *A61P 39/00* | (2006.01) | |
| *A61K 31/455* | (2006.01) | |
| *A61K 36/05* | (2006.01) | |
| *A61K 36/062* | (2006.01) | |

(52) U.S. Cl.
CPC .......... *A61K 36/815* (2013.01); *A61K 31/455* (2013.01); *A61K 36/05* (2013.01); *A61K 36/062* (2013.01); *A61P 39/00* (2018.01); *A61K 2236/331* (2013.01); *A61K 2236/333* (2013.01); *A61K 2236/51* (2013.01)

(58) Field of Classification Search
None
See application file for complete search history.

(56) References Cited

FOREIGN PATENT DOCUMENTS

| CN | 107441236 A |   | 12/2017 |
|---|---|---|---|
| CN | 110237104 A |   | 9/2019 |
| CN | 111109555 A |   | 5/2020 |
| CN | 111602760 A | * | 9/2020 |

OTHER PUBLICATIONS

El-Baz (International Journal of Pharmacy and Pharmaceuticals (2017), vol. 9, No. 1. pp. 192-198).*
Search Report for corresponding priority application CN2021109904707, filed Aug. 26, 2021.
First Office Action issued by the State IP Office of People's Republic of China, undated. Chinese original and English translation.
"Goji General History", Sunlight Press, Jun. 2019, pp. 464-465. Chinese original and English translation.

* cited by examiner

*Primary Examiner* — Susan Hoffman
(74) *Attorney, Agent, or Firm* — Hoffmann & Baron, LLP (57) ABSTRACT

The invention relates to the field of health food technologies, and particularly to a composition and an application thereof in preparing a product for protecting mitochondria. The invention provides a composition, the raw materials of which include *Haematococcus pluvialis*, *Lycium ruthenicum*, *Cordyceps militaris* and nicotinamide. The composition has the effects of improving an oxidative stress level under a mitochondrial dysfunction and delaying mitochondrion-related aging. Compared with a single constituent, constituents in the composition cooperate with each other to produce a synergistic effect, which significantly improves an effect of protecting a mitochondrial function.

5 Claims, 5 Drawing Sheets

COMPOSITION AND APPLICATION THEREOF IN PREPARING PRODUCT FOR PROTECTING MITOCHONDRIA

CROSS-REFERENCE TO RELATED APPLICATIONS

This application claims the benefit of priority to Chinese Patent Application No. 202110990470.7, filed Aug. 26, 2021, the entire disclosure of which is incorporated herein by reference.

TECHNICAL FIELD

The invention relates to the field of health food technologies, and particularly to a composition and an application thereof in preparing a product for protecting mitochondria.

BACKGROUND

Mitochondria are organelles which exist in most cells and are covered by two layers of membranes, and are a structure for producing energy in cells. The mitochondria have a function of energy conversion, and are a place where eukaryotic organisms undergo oxidative metabolism, and a place where sugars, fats and amino acids are finally oxidized to release energy. The mitochondria are also places of tricarboxylic acid cycle and oxidative phosphorylation. In addition, the mitochondria also have the functions of storing calcium ions, regulating membrane potential, controlling programmed cell death, cell proliferation and cell metabolism, and synthesizing cholesterol and certain heme, and the like. Studies have proved that a mitochondrial dysfunction is associated with many physiological and pathological processes, such as aging, Parkinson's disease, diabetes, neuropathic pain, and other diseases.

At present, a mitochondrial function is mainly evaluated by detecting oxygen consumption, a membrane potential, ATP level and a reactive oxygen species level of the mitochondria. Slc25a46−/− mice are karyogene Slc25a46 (which encodes a mitochondrial outer membrane protein) knockout mice, and the mice are mainly characterized by life shortening by less than two months, the obvious impairment of exercise ability, the atrophy of gastrocnemius muscle and the imbalance of redox levels in brain and liver. A mechanism of various organ dysfunctions of the Slc25a46 knockout mice may be related to the mitochondrial dysfunction, and mainly shows the impairment of a mitochondrial structure and the reduction of a respiratory chain enzyme activity. According to the present invention, a function of the composition or the extract of the invention is verified by taking the Slc25a46 gene knockout mice undergoing mitochondrial damage and aging as model animals of the mitochondrial dysfunction. This model has obvious phenotypic advantages (including short life, small size, slow movement, mitochondrial dysfunction, oxidative stress damage, stable phenotype, clear mechanism, high repeatability, short modeling time and many other advantages). In practical application, this mouse model is helpful for studying an action mechanism of the aging in energy metabolism, mitochondrial structure, mitochondrial function, oxidative stress, etc., and evaluating an effect of health food for delaying aging, thus having very obvious advantages.

SUMMARY

In view of this, the technical problem to be solved by the invention is to provide a composition and an application thereof in preparing a product for protecting mitochondria, and the composition can improve an oxidative stress level under a mitochondrial dysfunction and delay mitochondrion-related aging, and can be used for preparing a product for protecting a mitochondrial function.

The composition provided by the invention includes raw materials of *Haematococcus pluvialis*, *Lycium ruthenicum*, *Cordyceps militaris* and nicotinamide.

In the invention, a mass ratio of the *Haematococcus pluvialis* to the *Lycium ruthenicum*, the *Cordyceps militaris* and the nicotinamide is (100~450):(200~800):(50~150):(0.1~10).

In an embodiment of the invention, the mass ratio of the *Haematococcus pluvialis* to the *Lycium ruthenicum*, the *Cordyceps militaris* and the nicotinamide is (120~400):(300~700):(60~120):(0.1~5).

In some embodiments, the mass ratio of the *Haematococcus pluvialis* to the *Lycium ruthenicum*, the *Cordyceps militaris* and the nicotinamide is (150~300):(400~650):(80~110):(0.1~0.5).

In some specific embodiments, the mass ratio of the *Haematococcus pluvialis* to the *Lycium ruthenicum*, the *Cordyceps militaris* and the nicotinamide is 180:435:100:0.2.

The constituents in the composition of the invention, including the *Haematococcus pluvialis*, the *Lycium ruthenicum*, the *Cordyceps militaris* and the nicotinamide, cooperate with each other to produce a synergistic effect, which significantly improves an effect of protecting a mitochondrial function.

The invention further provides an extract prepared from the composition.

A preparation method of the extract of the invention includes the following steps of:
  extracting *Haematococcus pluvialis* with ethanol to prepare a *Haematococcus pluvialis* extract;
  preparing a *Lycium ruthenicum* extract by water extraction;
  extracting *Cordyceps militaris* with water to prepare a *Cordyceps militaris* extract; and
  mixing the *Haematococcus pluvialis* extract, the *Lycium ruthenicum* extract and the *Cordyceps militaris* extract with nicotinamide to prepare the extract.

In the invention, the step of extracting the *Haematococcus pluvialis* with ethanol includes: refluxing and extracting the *Haematococcus pluvialis* with 80 times of 70 wt % ethanol by weight for 4 hours;
  the step of preparing the *Lycium ruthenicum* extract by water extraction includes: refluxing and extracting the *Lycium ruthenicum* with 10 parts of water by weight for 5 hours; and
  the step of extracting the *Cordyceps militaris* with water includes: refluxing and extracting a fruiting body of the *Cordyceps militaris* with 8 times of boiling water by weight for 3 times, with each time lasting for 1.5 hours, and combining extracting solutions for concentration and drying.

An application of the composition of the invention, or the extract, or the extract prepared by the extraction method in preparing a product for improving an oxidative stress level and delaying aging is provided.

In the invention, the improving the oxidative stress level is to improve an oxidative stress level under a mitochondrial dysfunction, which mainly includes: improving an SOD enzyme activity.

In the invention, the delaying aging is to improve an NAMPT enzyme activity under the mitochondrial dysfunction.

In the invention, the delaying aging is to improve a protein expression level of a respiratory chain complex under the mitochondrial dysfunction.

In the invention, the mitochondrial dysfunction is caused by deletion or low expression of a Slc25a46 gene.

The Slc25a46 gene is a gene encoding a mitochondrial outer membrane protein, and plays an important role in mitochondrial dynamics. According to this invention, a function of the composition or the extract of the invention is verified by Slc25a46 gene knockout mice undergoing mitochondrial damage and aging. This model has obvious phenotypic advantages (including short life, small size, slow movement, mitochondrial dysfunction, oxidative stress damage, stable phenotype, clear mechanism, high repeatability, short modeling time and many other advantages). In practical application, this mouse model is helpful for studying an action mechanism of the aging in energy metabolism, mitochondrial structure, mitochondrial function, oxidative stress, etc., and evaluating an effect of health food for delaying aging, thus having very obvious advantages.

In the invention, an application of the composition, or the extract, or the extract prepared by the extraction method in preparing a product for protecting mitochondria is provided.

The invention further provides a product for protecting mitochondria, including the composition, or the extract, or the extract prepared by the extraction method of the invention.

In the invention, the product is a food, a drug or a health care product.

The food for protecting mitochondria includes the composition, or the extract, or the extract prepared by the extraction method of the invention, and an acceptable adjuvant in the food.

The health care product for protecting mitochondria includes the composition, or the extract, or the extract prepared by the extraction method of the invention, and an acceptable adjuvant in the health care product.

The drug for protecting mitochondria includes the composition, or the extract, or the extract prepared by the extraction method of the invention, and a pharmaceutically acceptable adjuvant.

The pharmaceutically acceptable adjuvant is one or a mixture of two or more of a fruit powder, a food flavor, a sweetening agent, a sour agent, a filler, a lubricant, a preservative, a suspending agent, a colorant, a diluent, an emulsifier, a disintegrant or a plasticizer.

A dosage form of the drug or the health care product is a tablet, a pill, an oral liquid, a capsule, a syrup, a dripping pill or a granule. Preferably, the capsule is a hard capsule or a soft capsule. Preferably, the tablet is an oral tablet or an oral cavity tablet. The oral tablet refers to a tablet for oral administration, the drug in most tablets is absorbed by a gastrointestinal tract, and the drug in some tablets plays a local role in the gastrointestinal tract. In some embodiments provided by the invention, the oral tablet is a common compressed tablet, a dispersible tablet, an effervescent tablet, a chewable tablet, a coated tablet or a sustained and controlled release tablet.

The invention provides a composition, the raw materials of which include *Haematococcus pluvialis*, *Lycium ruthenicum*, *Cordyceps militaris* and nicotinamide. The composition has the effects of improving the oxidative stress level under the mitochondrial dysfunction and delaying the mitochondrion-related aging. Compared with a single constituent, the constituents in the composition cooperate with each other to produce a synergistic effect, which significantly improves an effect of protecting the mitochondrial function.

DETAILED DESCRIPTION

This invention provides a composition and an application thereof in preparing a product for protecting mitochondria. Those skilled in the art may learn from the disclosure herein and appropriately improve the parameter for realization. It should be particularly pointed out that all similar substitutions and modifications are obvious to those skilled in the art, and the substitutions and modifications are all considered to be included in the invention. The method and the application of the invention have been described through the preferred examples, and it is obvious that relevant personnel are able to modify or appropriately alter and combine the method and the application herein without departing from the content, spirit and scope of the present invention to realize and apply the technology of the present invention.

Test materials used in this invention are all ordinary commercial products, and may all be purchased in the market.

In a specific example, during application of a composition formula and each single raw material in a natural product composition with a function of protecting mitochondria of the invention, in-vivo experiments are carried out through model animals of Slc25a46 gene knockout mice undergoing mitochondrial damage to explore protection of a mitochondrial function of the composition formula and the single raw material in the natural product composition. A mitochondrial dysfunction may cause decrease of a mitochondrial membrane potential, reduction of ATP synthesis, increase of oxidative stress, etc., and may directly or indirectly affect a normal function of a whole cell, and then affect an organ such as a liver (a central station of in-vivo metabolism) and a brain (an organ of a body with a highest metabolic rate, wherein most energy needed is obtained through aerobic metabolism) to a certain extent.

Specifically, in addition to a cytotoxicity (MTT) experiment carried out on the composition formula and the single raw material first, effects of the composition formula and the single raw material in the natural product composition are evaluated through an oxidative stress and an anti-aging enzyme activity of the above animal model. In order to evaluate an oxidative stress level and an ability of delaying aging, an SOD (superoxide dismutase) activity in brain and liver tissues, and a protein expression level of a mitochondrial respiratory chain complex and an NAMPT (nicotinamide phosphoribosyltransferase) activity in the liver tissue of the Slc25a46−/− mice after intervention with the composition formula and the single raw material are detected.

The invention is further described hereinafter with reference to the example:

Example

A composition was prepared according to the following composition formula: a mass ratio of *Haematococcus pluvialis* to *Lycium ruthenicum*, *Cordyceps militaris* and nicotinamide was 180:435:100:0.2.

A preparation method included the following steps.
1. Preparation method of *Haematococcus pluvialis* extract: 1 part of the *Haematococcus pluvialis* by weight was added into 80 times of 70 wt % ethanol by weight, refluxed and extracted in a water bath at 40° C. for 4 hours, sucked and filtered, concentrated and then dried in vacuum, so that the *Haematococcus pluvialis* extract was prepared.
2. Preparation method of *Lycium ruthenicum* extract: the *Lycium ruthenicum* was cleaned, 1 part of the *Lycium ruthenicum* by weight was added into 10 parts of water by weight, refluxed and extracted in a water bath at 50° C. for 5 hours, and filtered, and an obtained precipitate was subjected to spray drying, so that *Lycium ruthenicum* extract was prepared.
3. Preparation method of *Cordyceps militaris* powder: a fruiting body of the *Cordyceps militaris* was refluxed and extracted with 8 times of boiling water by weight for 3 times, with each time lasting for 1.5 hours, and extracting solutions were collected, concentrated into an extract (with a specific gravity of 1.05 to 1.07) in vacuum at 69° C.±3° C., then subjected to spray drying (with an air inlet temperature of 140° C. to 190° C. and an air outlet temperature of 70° C. to 90° C.), and sieved with an 80-mesh sieve.

The *Haematococcus pluvialis* extract, the *Lycium ruthenicum* extract and the *Cordyceps militaris* extract were mixed with the nicotinamide according to the formula to prepare the composition.

Comparative Example 1

Preparation method of *Haematococcus pluvialis* extract: 1 part of *Haematococcus pluvialis* by weight was added into 80 times of 70 wt % ethanol by weight, refluxed and extracted in a water bath at 40° C. for 4 hours, sucked and filtered, concentrated and then dried in vacuum, so that the *Haematococcus pluvialis* extract was prepared.

Comparative Example 2

Preparation method of *Lycium ruthenicum* extract: *Lycium ruthenicum* was cleaned, 1 part of the *Lycium ruthenicum* by weight was added into 10 parts of water by weight, refluxed and extracted in a water bath at 50° C. for 5 hours, and filtered, and an obtained precipitate was subjected to spray drying, so that *Lycium ruthenicum* extract was prepared.

Comparative Example 3

Preparation method of *Cordyceps militaris* powder a fruiting body of *Cordyceps militaris* was refluxed and extracted with 8 times of boiling water by weight for 3 times, with each time lasting for 1.5 hours, and extracting solutions were collected, concentrated into an extract (with a specific gravity of 1.05 to 1.07) in vacuum at 69° C.±3° C., then subjected to spray drying (with an air inlet temperature of 140° C. to 190° C. and an air outlet temperature of 70° C. to 90° C.), and sieved with an 80-mesh sieve.

Comparative Example 4

Commercial food-grade nicotinamide was purchased and used.

Verification of Effect
1. Acquisition and Culture of Mouse Embryonic Fibroblast (MEF)

The MEF cells were derived from wild-type fetal mice (WT) and Slc25a46 homozygous fetal mice (Slc25a46−/−). Pregnant mice were anesthetized and killed, and dissected to obtain mouse embryos, and bodies of fetal mice were obtained, and washed with PBS for 3 times. Clean mouse embryonal tissues were transferred into a culture dish, and cut into pieces, 2 mL of trypsin was added into the tissue pieces, and continuously cut into pieces for several minutes. Then, 5 mL of trypsin was added into the culture dish above, and blown up and down with a straw vigorously, and the culture dish was put into an incubator for incubation for 20 minutes to 30 minutes. The tissues cut into pieces were taken out of the incubator, and added with about 20 mL of MEF medium. A tissue mixture was transferred into each flask and placed into an incubator for overnight incubation. Then, growth of fibroblasts was observed regularly and the culture medium was replaced. When the fibroblasts covered 90% of the culture flask, the mouse embryonic fibroblasts were collected for subsequent experiment.

II. In-Vitro Cytotoxicity Experiment of Natural Product Composition Formula of the Invention MTT Experiment:

100 uL of WT mouse cells and Slc25a46−/− mouse cells with a cell concentration of $3.5 \times 10^5$ cells/mL were inoculated into a 96-well plate, and cultured in a $CO_2$ incubator at 37° C. for 24 hours. A series of test solutions containing the composition formulae (Example) and the single raw material (Comparative examples 1 to 4) in the natural product composition with different concentrations of 0 μg/mL, 62.5 μg/mL, 125 μg/mL, 250 μg/mL, 500 μg/mL, 1,000 μg/mL and 2,000 μg/mL were used to act on the cells for 24 hours, 20 μL of MTT solution with a concentration of 5 mg/mL was added into each well, and continuously cultured at a constant temperature for 4 hours, a supernatant was discarded, and 150 μL of DMSO was added into each well to fully dissolve a formazan crystal. An absorbance at 570 nm was detected with a multi-functional microplate scanner, and effects of test solutions with different concentrations on cell viability were calculated with a blank control as 100%.

Figure 1A:
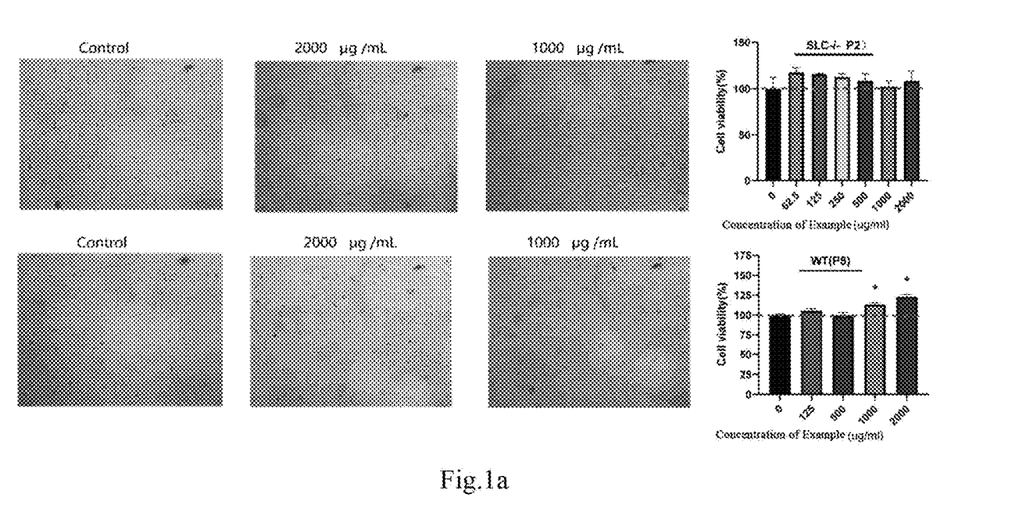
FIG. 1a shows an effect of Example on a morphology and a vitality of Slc25a46−/− and WT mouse embryonic fibroblasts.

As shown in FIG. 1a, the composition formula in Example has no effect on cell morphology. The composition formula at 125 μg/mL to 2,000 μg/mL is nontoxic to the cells, and the composition formula at 1,000 μg/mL to 2,000 μg/mL promotes growth of the WT cells, with a concentration effect.

Figure 1B:
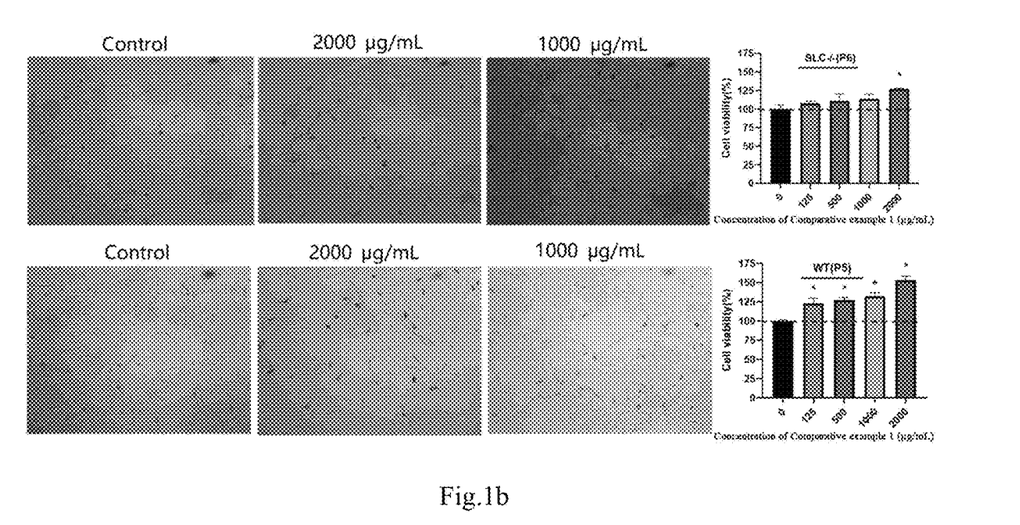
FIG. 1b shows an effect of Comparative example 1 on the morphology and the vitality of the Slc25a46−/− and WT mouse embryonic fibroblasts.

As shown in FIG. 1b, the *Haematococcus pluvialis* in Comparative example 1 has no effect on the cell morphology. The *Haematococcus pluvialis* at 125 μg/mL to 2,000 μg/mL can promote growth of the Slc25a46−/− cells and the WT cells, with a concentration effect.

Figure 1C:
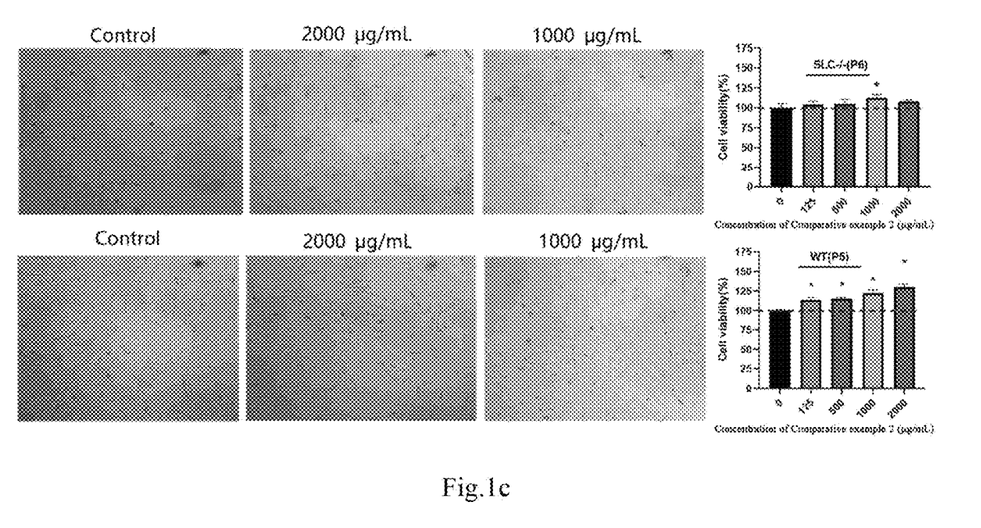
FIG. 1c shows an effect of Comparative example 2 on the morphology and the vitality of the Slc25a46−/− and WT mouse embryonic fibroblasts.

As shown in FIG. 1c, the *Lycium ruthenicum* in Comparative example 2 has no effect on the cell morphology. The *Lycium ruthenicum* at 1000 μg/mL can promote growth of the Slc25a46−/− cells, without a concentration effect. The *Lycium ruthenicum* at 125 μg/mL to 2,000 μg/mL promotes growth of the WT cells, with a concentration effect.

Figure 1D:
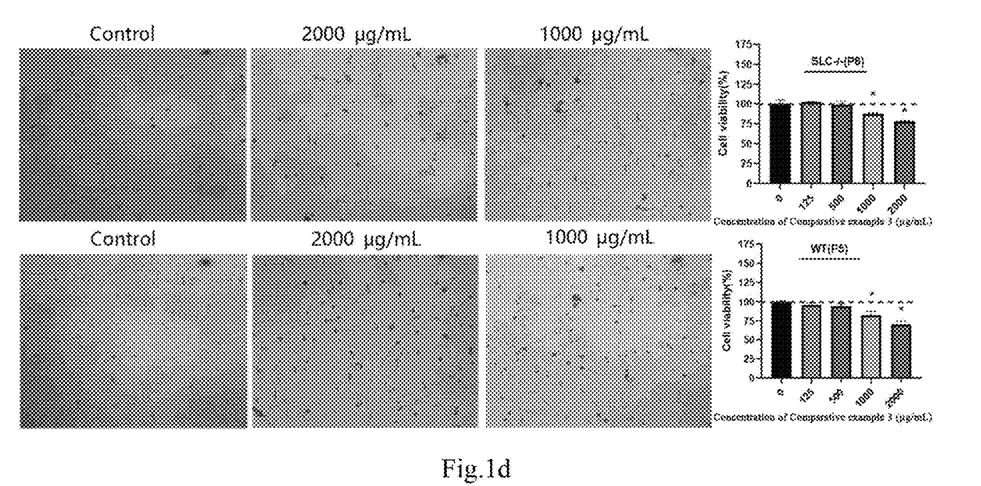
FIG. 1d shows an effect of Comparative example 3 on the morphology and the vitality of the Slc25a46−/− and WT mouse embryonic fibroblasts.

As shown in FIG. 1d, the *Cordyceps militaris* in Comparative example 3 has no effect on the cell morphology. The *Cordyceps militaris* at a low concentration (ranging from 125 μg/mL to 500 μg/mL) has no obvious effect on cell growth. The *Cordyceps militaris* at a high concentration (ranging from 1,000 μg/mL to 2,000 μg/mL) has an inhibiting effect.

Figure 1E:
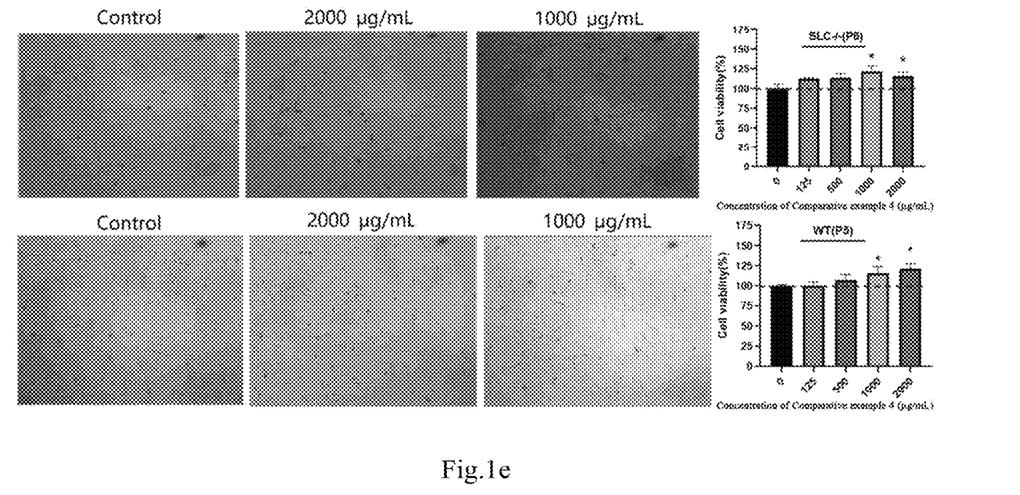
FIG. 1e shows an effect of Comparative example 4 on the morphology and the vitality of the Slc25a46−/− and WT mouse embryonic fibroblasts.

As shown in FIG. 1e, the nicotinamide in Comparative example 4 has no effect on the cell morphology. The nicotinamide at 1,000 μg/mL to 2,000 μg/mL promotes growth of the Slc25a46−/− cells and the WT cells, without a concentration effect.

In terms of cell morphology, Example (composition formula) and Comparative examples 1 to 4 (single raw material formula) in the same concentration range have no obvious effects on morphology of the Slc25a46−/− cells and morphology of the WT cells. In terms of cell viability, Example (composition formula) at 125 μg/mL to 2,000 μg/mL has no effect on a viability of the Slc25a46−/− cells, and Example (composition formula) at a high concentration can promote proliferation of the WT cells. Comparative examples 1, 2 and 4 of the single raw material formula at 125 μg/mL to 2,000 μg/mL have no effect on the viability of the Slc25a46−/− cells and a viability of the WT cells, and Comparative examples 1, 2 and 4 of the single raw material formula at a high concentration can also promote proliferation of the WT cells. However, although Comparative example 3 (*Cordyceps militaris*) at a low concentration has no effect on the viability of the Slc25a46−/− cells and the viability of the WT cells, Comparative example 3 (*Cordyceps militaris*) at a high concentration has an inhibiting effect on the Slc25a46−/− cells and the WT cells, showing a toxic effect, so that a dosage should be concerned in use. Example is composed of Comparative examples 1 to 4 in a certain proportion. Therefore, under a same total concentration, contents of the *Haematococcus pluvialis*, the *Lycium ruthenicum*, the *Cordyceps militaris* and the nicotinamide in Example are respectively lower than those of the raw materials in the corresponding Comparative examples. Based on results of contents of the composition formula (Example) and the single raw material formula (Comparative examples 1 to 4) and effects of the composition formula (Example) and the single raw material formula (Comparative examples 1 to 4) on the cell morphology and vitality, it is found that Example shows better safety and stability than Comparative examples, which shows a superiority of a scientific proportion of the composition formula, and the safety of the composition formula is also explored.

III. In-Vivo Mitochondrial Function Protection Experiment of in Natural Product Composition Formula of the Invention 1. Experimental Animals Animal experimental subjects were Slc25a46 knockout (Slc25a46−/−) mice of 1 month old, which were divided into a blank solvent control group (3 mice) and experimental groups (4 mice in each group). Under a same SPF level, the mice were fed with a full-nutrient feed prepared according to an AIN93G formula of Jiangsu Xietong Biology Co., Ltd., and subjected to intragastric administration every day, which lasted for a period of 10 days. The experimental groups were administered intragastrically with a test substance of the composition formula of Example by 400 mg/kg every day, a test substance of Comparative example 1 by 100 mg/kg every day, a test substance of Comparative example 2 by 244 mg/kg every day, a test substance of Comparative example 3 by 56 mg/kg every day, and a test substance of Comparative example 4 by 500 mg/kg every day. The blank solvent control group was administered intragastrically with solvent water. After the intragastric administration experiment, brain tissues and liver tissues of the mice were collected for physiological and biochemical detections respectively, and an oxidative stress level and an ability of delaying aging were analyzed.

2. Biochemical Detection of Brain Tissues and Liver Tissues of Mice 9 times volume of ice normal saline was added according to a ratio of a tissue weight (g) to a tissue volume (ml) of 1:9, and the tissues were cut into pieces with a surgical scissor, prepared into 10% tissue homogenate with a homogenizer (the homogenation lasted 10 seconds once, and was continuously carried out for 3 times to 5 times at intervals of 5 seconds on ice), and centrifuged at 2500 rpm to 3000 rpm for 10 minutes. A supernatant was taken for subsequent determination. The determination was operated in strict accordance with an instruction of a superoxide dismutase (SOD) determination kit (article number: A001-3, WST-1 method, Nanjing Jiancheng Bioengineering Institute) to detect an SOD enzyme activity in the brain and liver homogenates, and statistical analysis was made with Prism software.

Figure 2:
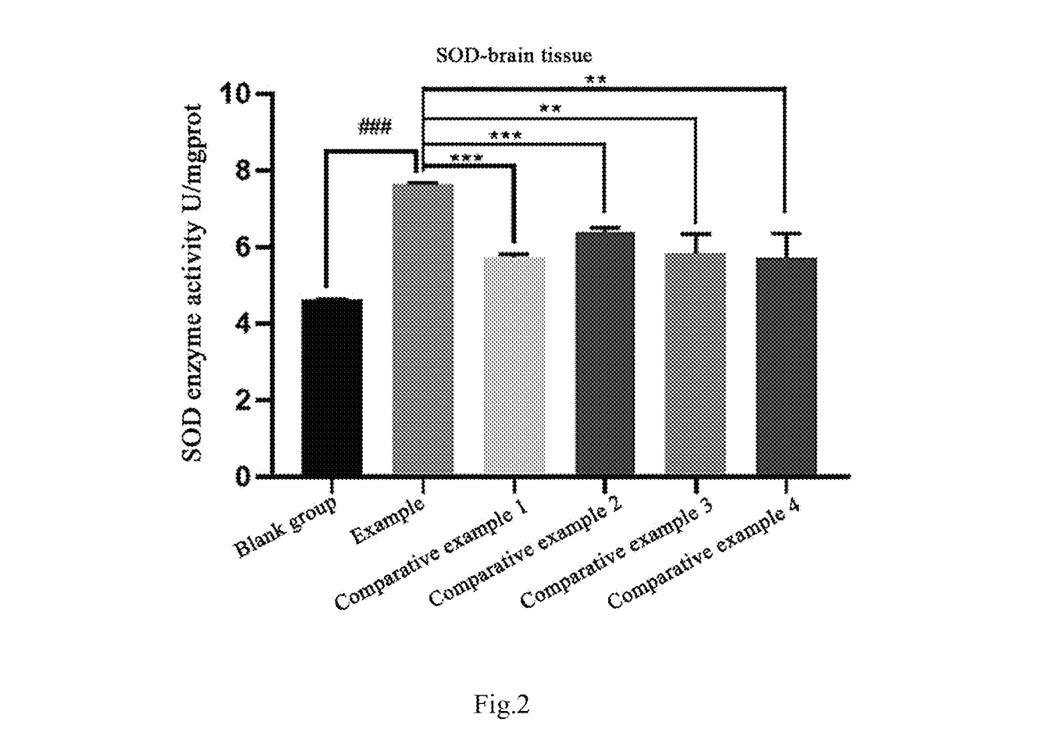
FIG. 2 shows detection results of an SOD enzyme activity in brain tissues of Slc25a46−/− mice in a blank group, an intervention group of Example and intervention groups of Comparative examples 1 to 4.
Figure 3:
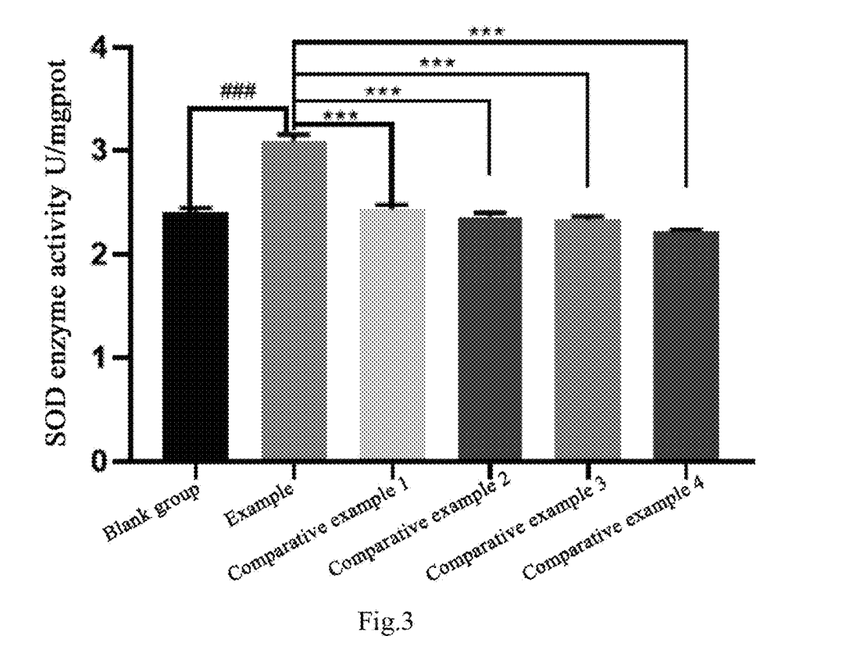
FIG. 3 shows detection results of an SOD enzyme activity in liver tissues of the Slc25a46−/− mice in the blank group, the intervention group of Example and the intervention groups of Comparative examples 1 to 4.

The higher the SOD enzyme activity was, the better the antioxidant effect was. As shown in Table 1 and FIG. 2 and FIG. 3, the SOD enzyme activity in the brain tissues and the liver tissues of the intervention group of the composition formula (Example) is significantly higher than that of the blank group (p<0.001), which indicates that the intervention of the composition formula can effectively improve an antioxidant level in the brain tissues and the liver tissues of the Slc25a46−/− homozygous mice. Meanwhile, the SOD enzyme activity in the brain tissues and the liver tissues of the mice in the intervention group of Example is significantly higher than that in groups of Comparative examples 1 to 4 (p<0.01). However, there is no significant difference between two of the groups of Comparative examples. Based on the above analysis, it is shown that the composition formula has good antioxidant ability, and an antioxidant effect of the composition formula is significantly higher than that of the single raw material.

3. Detection of Protein Level Expression of Mitochondrial Respiratory Chain Complex in Liver Tissues of Mice 100 mg of liver tissues of the mice were added with a lysis solution containing protease and a phosphorylase inhibitor in proportion to lyse tissue cells. Proteins were collected and extracted by a conventional method, and a concentration of protein samples was detected by a BCA kit. SDS-PAGE electrophoresis gel was prepared, protein electrophoresis was implemented, a membrane was transferred by a wet process, and sealing was carried out. Antibody incubation: corresponding to a size of a protein marked by protein Marker, an NC membrane was cut according to a molecular weight of a target protein, the cut NC membrane was placed in an antibody incubation box, and a primary antibody (OXPHOS, 1:1000) solution was added to completely immerse a surface of the NC membrane. Then, the incubation box was placed on a shaking table in a cold storage at 4 L for overnight incubation, and the primary antibody solution was recovered the next morning and put back into a refrigerator at −20□ for storage. The NC membrane was washed with a TBST buffer for 3 times, with each time lasting for about 10 minutes. After washing, a secondary antibody was added, and incubated on the shaking table at a room temperature for about 1.5 hours. Then, the NC membrane was washed with the TBST buffer for 3 times. A protein developing instrument was precooled, and a protein developing solution A:B was prepared into a developing working solution according to a volume ratio of 1:1 for current use. Excess buffer on the membrane was absorbed with filter paper first, the NC membrane was put into a container containing the developing working solution to be immersed in the dark, and then the membrane was put into the instrument for exposure imaging. An exposure function of optimal time for a single image was selected, an exposed protein strip map was kept and data was analyzed with software Image J, and a protein expression content was calculated according to a gray value.

Figure 4:
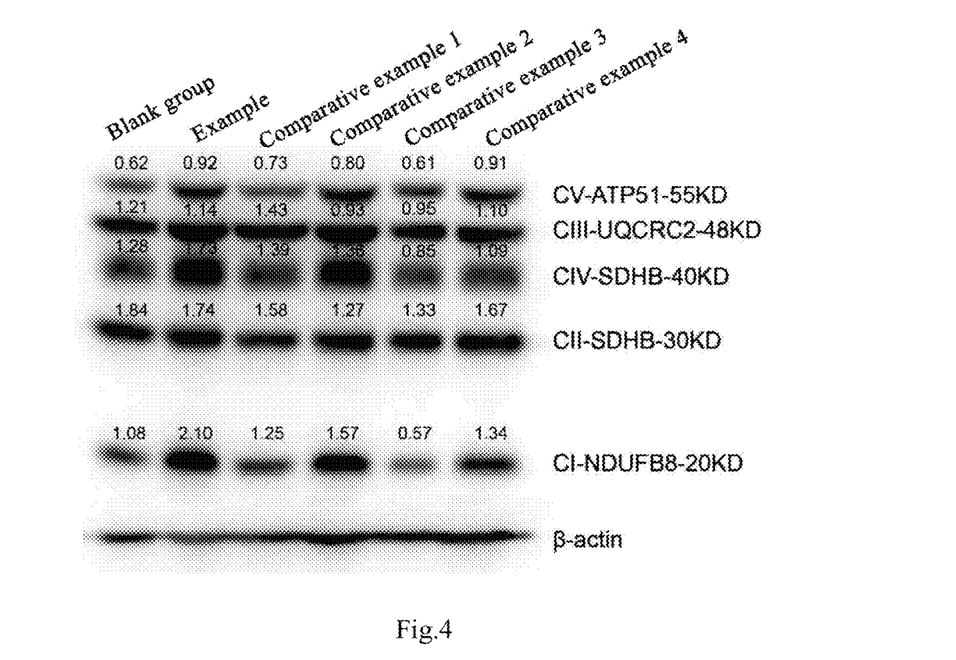
FIG. 4 shows detection results of a protein expression level of a mitochondrial respiratory chain complex in the liver tissues of the Slc25a46−/− mice in the blank group, the intervention group of Example and the intervention groups of Comparative examples 1 to 4.
Figure 5:
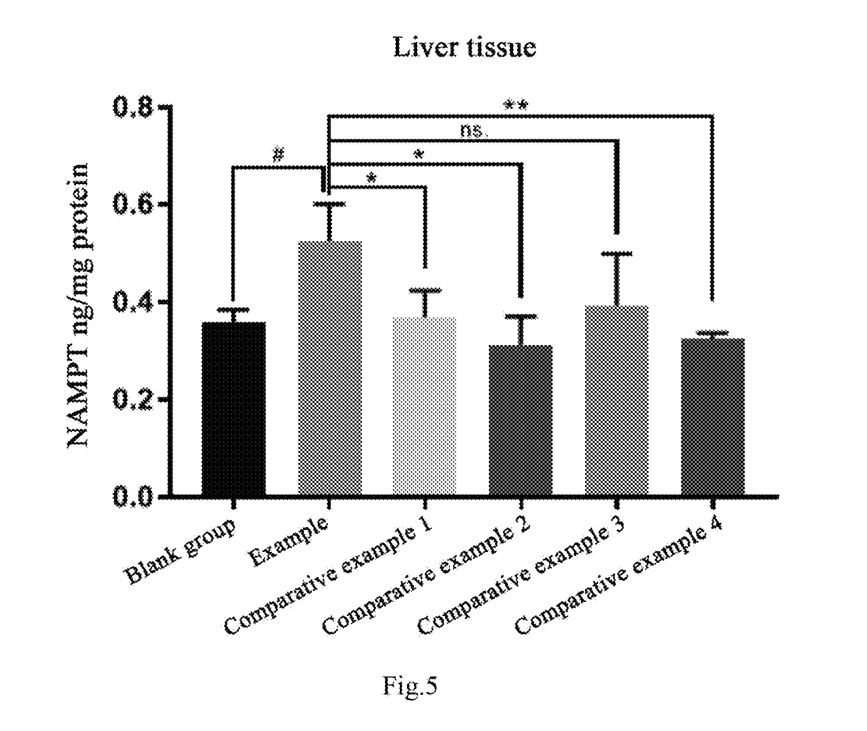
FIG. 5 shows detection results of an NAMPT enzyme activity in the liver tissues of the Slc25a46−/− mice in the blank group, the intervention group of Example and the intervention groups of Comparative examples 1 to 4.

A function of the respiratory chain (complex I-V) represented a basic function of mitochondria. The respiratory chain was a continuous reaction system formed by arranging a series of hydrogen transfer reactions and electron transfer reactions in a certain sequence. A main function of the respiratory chain was to generate energy through a hydrogen carrier and an electron carrier in the respiratory chain and a series of oxidation-reduction processes. As shown in FIG. 4 (marked value in the drawing=gray level of complex/gray level of β-actinin in same column, which is a relative value), compared with the blank group, protein levels of complexes I, III, IV and V of the mitochondrial respiratory chain in the intervention group of Example are obviously increased, especially the complexes I, IV and V, which indicates that Example can improve functions of electron transfer and ATP synthesis of the damaged mitochondrial respiratory chain. Protein level expressions of the respiratory chain complexes I to V in the raw material intervention groups (Comparative examples 1 to 4) are slightly higher than that in the blank group, especially Comparative example 2 (*Lycium ruthenicum* group), but are all lower than that in the group of Example. To sum up, compared with Comparative examples, Example (composition formula) has a function of improving damaged mitochondria.

4. Detection Experiment of NAMPT Enzyme Activity in Liver Tissues of Mice

A certain amount of liver tissues of the mice were homogenized, and a supernatant was taken. Detection was operated in strict accordance with an instruction of a mouse nicotinamide phosphoribosyltransferase (NAMPT) ELISA detection kit (article number: JL24460, enzyme-linked immunosorbent assay, Jianglai Bio). Marker wells, blank wells and sample wells were provided, 50 μL of markers with different concentrations were added into the marker wells, 50 μL of to-be-tested sample was added into the sample wells, and 50 μL of sample diluent was added into the blank wells. 100 μL of horse radish peroxidase (HRP)-labeled detection antibody was added to each marker well, each blank well and each sample well, the reaction wells were sealed with a sealing plate membrane, and reaction was carried out in a water bath at 37□ for 60 minutes. A waste liquid was discarded, and patted dry on absorbent paper. A cleaning solution (350 μL) was filled in each well, and stood still for 1 minute. The cleaning solution was shaken off, and patted dry on absorbent paper. The plate was repeatedly washed in this way for 5 times. 50 μL of substrate A and 50 μL of substrate B were respectively added into each well, and an OD value of each well at a wavelength of 450 nm was measured within 15 minutes. Data was recorded, and statistical analysis was made with Prism software.

Nicotinamide phosphoribosyltransferase (NAMPT) was divided into intracellular and extracellular nicotinamide phosphoribosyltransferase, which was a rate-limiting enzyme for biosynthesis of NAD+, and played a very important role. Study found that increase of an NAMPT level could promote synthesis of NAD+, and played a role of delaying aging and prolonging life. As shown in Table 1 and FIG. 4, compared with the blank group, the NAMPT enzyme activity in the liver tissues of the mice in the group of Example is significantly higher than that in the blank group ($P<0.05$). Meanwhile, the NAMPT enzyme activity in the group of Example is significantly higher than that in the groups of Comparative examples 1, 2 and 4 ($P<0.05$), and there is no significant difference with the group of Comparative example 3. The above results show that Example (composition formula) has a potential effect of delaying aging and prolonging life, and the effect is better than that of the single raw material.

TABLE 1

| Grouping | Blank group | Example | Comparative example 1 | Comparative example 2 | Comparative example 3 | Comparative example 4 |
|---|---|---|---|---|---|---|
| SOD enzyme activity- Brain tissue (U/mgprot) | 4.63 ± 0.03### | 7.64 ± 0.05 | 5.73 ± 0.08*** | 6.41 ± 0.096*** | 5.84 ± 0.50** | 5.73 ± 0.63** |
| SOD enzyme activity- Liver tissue (U/mgprot) | 2.41 ± 0.04*** | 3.09 ± 0.06 | 2.44 ± 0.04*** | 2.36 ± 0.04*** | 2.34 ± 0.03*** | 2.22 ± 0.02*** |

TABLE 1-continued

| Grouping | Blank group | Example | Comparative example 1 | Comparative example 2 | Comparative example 3 | Comparative example 4 |
|---|---|---|---|---|---|---|
| NAMPT enzyme activity-Liver tissue (ng/mg protein) | 0.36 ± 0.03# | 0.53 ± 0.07 | 0.37 ± 0.05* | 0.31 ± 0.06* | 0.39 ± 0.11 | 0.32 ± 0.01** |

Note:
blank group vs Example,
'#', $p < 0.05$;
'##', $p < 0.01$;
'####', $p < 0.001$;
Example vs Comparative examples,
'*', $p < 0.05$;
'**', $p < 0.01$;
'***' $p < 0.001$.

Based on the results of the MTT toxicity experiment, the SOD enzyme activity experiment, the mitochondrial complex protein level expression experiment and the NAMPT enzyme activity experiment, it is indicated that the composition formula has no effect on a morphology of cells subjected to mitochondria damage (Slc25a46−/−) and a morphology of normal cells (WT) within a certain concentration range, and can improve proliferation abilities of the damaged cells and the normal cells. The enzyme activity of the antioxidase SOD, the protein level expression of the mitochondrial respiratory chain complex, and the enzyme activity of NAMPT promoting synthesis of NAD+ in the tissues of the Slc25a46−/− mice after intervention are improved, thus improving the oxidative stress level under the dysfunction and the aging related to mitochondrial damage, and the composition may be used for preparing a product with a mitochondrial protection function. Meanwhile, by comparing performances of the composition formula and the single raw material in the above detection indexes, it is found that the effect of the composition formula is safer, more stable and more effective than that of the single raw material, which shows the importance and scientificity of selection and proportion of raw materials of the composition formula.

The above is merely the preferred implementations of the invention, and it should be pointed out that those of ordinary skills in the art may further make improvements and decorations without departing from the principle of the invention, and these improvements and decorations should also be regarded as the scope of protection of the invention.

The invention claimed is:

1. A composition comprising an extract of *Haematococcus pluvialis*, *Lycium ruthenicum*, and *Cordyceps militaris* with nicotinamide; wherein the mass ratio of the *Haematococcus pluvialis* to the *Lycium ruthenicum*, the *Cordyceps militaris* and the nicotinamide is (100~450):(200~800):(50~150):(0.1~10);

wherein the extract of *Haematococcus pluvialis*, *Lycium ruthenicum*, *Cordyceps militaris* are ethanol extract of *Haematococcus pluvialis*, water extract of *Lycium ruthenicum* and water extract of *Cordyceps militaris*.

2. A product for improving mitochondrial dysfunction, comprising the composition according to claim 1.

3. A composition comprising an extract of *Haematococcus pluvialis*, *Lycium ruthenicum* and *Cordyceps militaris* with nicotinamide according to claim 1, wherein the mass ratio of the *Haematococcus pluvialis* to the *Lycium ruthenicum*, the *Cordyceps militaris* and the nicotinamide is (120~400):(300~700):(60~120):(0.1~5).

4. A composition comprising an extract of *Haematococcus pluvialis*, *Lycium ruthenicum* and *Cordyceps militaris* with nicotinamide according to claim 1, wherein the mass ratio of the *Haematococcus pluvialis* to the *Lycium ruthenicum*, the *Cordyceps militaris* and the nicotinamide is (150~300):(400~650):(80~110):(0.1~0.5).

5. A composition comprising an extract of *Haematococcus pluvialis*, *Lycium ruthenicum* and *Cordyceps militaris* with nicotinamide according to claim 1, wherein the mass ratio of the *Haematococcus pluvialis* to the *Lycium ruthenicum*, the *Cordyceps militaris* and the nicotinamide is 180:435:100:0.2.

* * * * *